(12) United States Patent
Yoon et al.

(10) Patent No.: US 7,638,653 B2
(45) Date of Patent: Dec. 29, 2009

(54) METHOD OF PREPARING PHOSPHONIUM COMPOUND FOR CYCLIC OLEFIN POLYMERIZATION

(75) Inventors: Sungcheol Yoon, Daejeon (KR); Young Chul Won, Suwon (KR); Young Whan Park, Daejeon (KR); Sung Ho Chun, Daejeon (KR); Dai Seung Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 449 days.

(21) Appl. No.: 11/492,059

(22) Filed: Jul. 25, 2006

(65) Prior Publication Data

US 2007/0027277 A1 Feb. 1, 2007

(30) Foreign Application Priority Data

Jul. 26, 2005 (KR) ............ 10-2005-0067830
Jul. 25, 2006 (KR) ............ 10-2006-0069534

(51) Int. Cl.
*C07F 9/02* (2006.01)
*C07F 15/04* (2006.01)
(52) U.S. Cl. ............................ 568/9; 556/13
(58) Field of Classification Search ............ 568/9; 556/13
See application file for complete search history.

(56) References Cited

U.S. PATENT DOCUMENTS

| | | | |
|---|---|---|---|
| 5,468,819 A | 11/1995 | Goodall et al. | |
| 5,569,730 A | 10/1996 | Goodall et al. | |
| 5,705,503 A | 1/1998 | Goodall et al. | |
| 5,912,313 A | 6/1999 | McIntosh, III et al. | |
| 6,031,058 A | 2/2000 | McIntosh, III et al. | |
| 6,455,650 B1 | 9/2002 | Lipian et al. | |

FOREIGN PATENT DOCUMENTS

WO  WO 2005/019277 A1  3/2005

OTHER PUBLICATIONS

Sen, A., et al., *Catalysis by Solvated Transition-Metal Cations. Novel Catalytic Transformations of Alkenes by Tetrakis (acetronitrile) palladium Dietrafluoroborate. Evidence for the Formation of Incipient Carbonium Ions of Intermediates*, Chandlee Laboratory, Dept. of Chemistry, 1981 American Chemical Society, pp. 4627-4629.
Hennis, A.D., et al., *Novel, Efficient, Palladium-Based System for the Polymerization of Norbornene Derivaties: Scope and Mechanism*, 2001 American Chemical Society, pp. 2802-2812.

*Primary Examiner*—Porfirio Nazario Gonzalez
(74) *Attorney, Agent, or Firm*—McKenna Long & Aldridge LLP

(57) ABSTRACT

Provided is a method of preparing a phosphonium compound by reacting a protic phosphonium compound represented by $[(R_1)-P(R_2)_a(R_2')_b]HX$ and a salt compound represented by [C][Ani]. Therefore, a phosphonium compound used as a cocatalyst for the preparation of a polar cyclic olefin polymer can be produced at high yield.

2 Claims, 1 Drawing Sheet

METHOD OF PREPARING PHOSPHONIUM COMPOUND FOR CYCLIC OLEFIN POLYMERIZATION

CROSS-REFERENCE TO RELATED PATENT APPLICATION

This application claims priorities from Korean Patent Application No. 10-2005-0067830, filed on Jul. 26, 2005, in the Korean Intellectual Property Office and Korean Patent Application No. 10-2006-0069534, filed on Jul. 25, 2006, in the Korean Intellectual Property Office, the disclosure of which are incorporated herein in its entirety by reference.

1. Field of The Invention

The present invention relates to a method of preparing a phosphonium compound, and more particularly, to a method of preparing a phosphonium compound used as a cocatalyst in a catalyst system for the polymerization of cyclic olefin monomers having polar functional groups.

2. Description of The Related Art

Cyclic olefin polymers, which are polymers composed of cyclic olefin monomers such as norbornene, have better transparency, heat resistance, and chemical resistance, and much lower birefringence and hygroscopicity, compared to conventional olefin-based polymers, and thus, can be widely applied as optical materials for CDs, DVDs, or POFs (Plastic Optical Fibers), information and electronic materials for capacitor films or low dielectrics, medical materials for low-absorbent syringes or blister packagings, etc.

Generally, in order for polymers to be used as information and electronic materials, the polymers need to have an adhesion to a surface of metal such as silicon, silicon oxide, silicon nitride, alumina, copper, aluminum, gold, silver, platinum, titanium, nickel, tantalum, or chromium. Thus, in order to adjust an adhesion to metal and electrical, optical, chemical, and physical characteristics of norbornene-based polymers, attempts have been made to incorporate polar functional groups to norbornene-based monomers. However, the incorporation of polar functional groups to norbornene-based monomers lowers catalyst activity or requires excess catalyst.

For example, U.S. Pat. No. 5,705,503 discloses a method of polymerizing a norbornene-based monomer having a polar functional group using a catalyst complex, ((Allyl)PdCl)$_2$/AgSbF$_6$. However, since an excess of the catalyst is used (1/100 to 1/250 relative to a monomer), a catalyst residue is left in excess in a finally obtained polymer. For this reason, the polymer may be degraded by thermal oxidation, and light transmittance may be lowered.

Furthermore, in polymerization of ester norbornene monomers in the presence of a cationic catalyst, [Pd(CH$_3$CN)$_4$][BF$_4$]$_2$, a polymerization yield is low and only exo-isomers are selectively polymerized [Sen, A.; Lai, T.-W. J. Am. Chem. Soc. 1981, Vol. 103, 4627-4629]. In polymerization of norbornenes having ester groups or acetyl groups, an excess of a catalyst is required (about 1/100 to 1/400 relative to a monomer), and thus, removal of a catalyst residue after the polymerization is difficult.

Meanwhile, it is reported that the use of a cocatalyst in cyclic olefin polymerization enhances catalyst activity. A compound capable of forming a strong sigma bond with metal, e.g., a neutral phosphine compound or an ammonium compound has been used as the cocatalyst.

For example, Sen, et al. [Organometallics 2001, Vol. 20, 2802-2812] reported ester norbornene polymerization catalyzed by [(1,5-cyclooctadiene)(CH$_3$)Pd(Cl)] and cocatalyzed by phosphine (PPh$_3$) and [Na]$^+$[B(3,5-(CF$_3$)$_2$C$_6$H$_3$)$_4$]$^-$, in which an excess of the catalyst was used (about 1/400 relative to the monomer), thereby yielding a polymer with a molecular weight of 6,500 (yield: 40% or less).

U.S. Pat. No. 6,455,650 discloses a method of polymerizing norbornene-based monomers having functional groups in the presence of a catalyst complex, [(R')$_z$M(L')$_x$(L'')$_y$]$_b$[WCA]$_d$ where phosphine and a hydrocarbyl (e.g., allyl)-containing hydrocarbon are used as ligands. However, a product yield in polymerization of norbornene-based monomers having polar functional groups (e.g., a carbonyl group) is very low (5%). Thus, the polymerization method disclosed in U.S. Pat. No. 6,455,650 is not suitable for production of polymers having polar functional groups (e.g., a carbonyl group). U.S. Pat. No. 5,468,819, No. 5,569,730, No. 5,912,313, and No. 6,031,058 also fail to meet a desired yield.

As described above, catalyst systems for polymerization of cyclic olefin monomers having polar functional groups include various cocatalysts. However, there still exists a problem of catalyst activity being lowered due to catalyst-monomer interaction.

The use of phosphonium compounds as substitutes for the above-illustrated cocatalysts has been suggested in WO 2005/019277, Korean Patent Application NO. 2004-0052612 and No. 2004-0074307, but these documents are silent about efficient preparation of the phosphonium compounds.

Therefore, it is necessary to develop a method of preparing easily and at a high yield a phosphonium compound used as a cocatalyst in a catalyst system for the polymerization of cyclic olefin monomers having polar functional groups.

SUMMARY OF THE INVENTION

The present invention provides a method of preparing a phosphonium compound used as a cocatalyst in a catalyst system for the preparation of cyclic olefins.

According to an aspect of the present invention, there is provided a method of preparing a phosphonium compound represented by Formula 1 below, contacting a phosphonium compound represented by Formula 2 below and a salt compound represented by Formula 3 below:

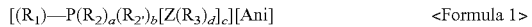
$$[(R_1)—P(R_2)_a(R_{2'})_b[Z(R_3)_d]_c][Ani] \quad \text{<Formula 1>}$$

wherein, a, b, and c are each an integer of 0 to 3 with proviso that a+b+c=3,

Z is oxygen, sulfur, silicon, or nitrogen, d is 1 when Z is oxygen or sulfur, is 2 when Z is nitrogen, and is 3 when Z is silicon, R$_1$ is hydrogen, alkyl, or aryl, R$_2$, R$_{2'}$, and R$_3$ are each independently hydrogen; straight or branched C$_{1-20}$ alkyl, alkoxy, allyl, alkenyl, or vinyl which is unsubstituted or substituted by a hydrocarbon(s), halogen(s) or C$_{1-20}$ haloalkyl; C$_{3-12}$ cycloalkyl which is unsubstituted or substituted by a hydrocarbon(s), halogen(s) or C$_{1-20}$ haloalkyl; C$_{6-40}$ aryl which is unsubstituted or substituted by a hydrocarbon(s), halogen(s) or C$_{1-20}$ haloalkyl; C$_{7-15}$ aralkyl which is unsubstituted or substituted by a hydrocarbon(s), halogen(s) or C$_{1-20}$ haloalkyl; C$_{3-20}$ alkynyl which is unsubstituted or substituted by a hydrocarbon(s), halogen(s) or C$_{1-20}$ haloalkyl; tri(straight or branched C$_{1-10}$ alkyl)silyl; tri(straight or branched C$_{1-10}$ alkoxy)silyl; tri(C$_{3-12}$ cycloalkyl)silyl where the C$_{3-12}$ cycloalkyl moiety is unsubstituted or substituted by a hydrocarbon(s), halogen(s) or C$_{1-20}$ haloalkyl; tri(C$_{6-40}$ aryl)silyl where the C$_{6-40}$ aryl moiety is unsubstituted or substituted by a hydrocarbon(s), halogen(s) or C$_{1-20}$ haloalkyl; tri(C$_{6-40}$ aryloxy)silyl where the C$_{6-40}$ aryloxy moiety is unsubstituted or substituted by a hydrocarbon(s), halogen(s) or C$_{1-20}$ haloalkyl; tri(straight or branched $C_{1-10}$ alkyl)siloxy; tri($C_{3-12}$ cycloalkyl)siloxy where the $C_{3-12}$ cycloalkyl moiety is unsubstituted or substituted by a hydrocarbon(s), halogen(s) or $C_{1-20}$ haloalkyl; or tri($C_{6-40}$ aryl)siloxy where the $C_{6-40}$ aryl moiety is unsubstituted or substituted by a hydrocarbon(s), halogen(s) or $C_{1-20}$ haloalkyl, and

[Ani] is borate, aluminate, [$SbF_6$]—, [$PF_6$]—, [$AsF_6$]—, perfluoroacetate ([$CF_3CO_2$]—), perfluoropropionate ([$C_2F_5CO_2$]—), perfluorobutyrate ([$CF_3CF_2CF_2CO_2$]—), perchlorate ([$ClO_4$]—), p-toluenesulfonate ([p-$CH_3C_6H_4SO_3$]—), [$SO_3CF_3$]—, boratabenzene, or carborane which is unsubstituted or substituted by halogen(s),

<Formula 2> wherein H is hydrogen, X is a halogen atom, and $R_1$, $R_2$, $R_{2'}$, a, and b are as defined above, and

<Formula 3> wherein C is alkaline metal or MgX, and [Ani] is as defined above.

The preparation method of the present invention may further include preparing the phosphonium compound of Formula 2 by treating a phosphine compound represented by Formula 4 below with an acid:

<Formula 4> wherein $R_1$, $R_2$, $R_{2'}$, a, and b are as defined above.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
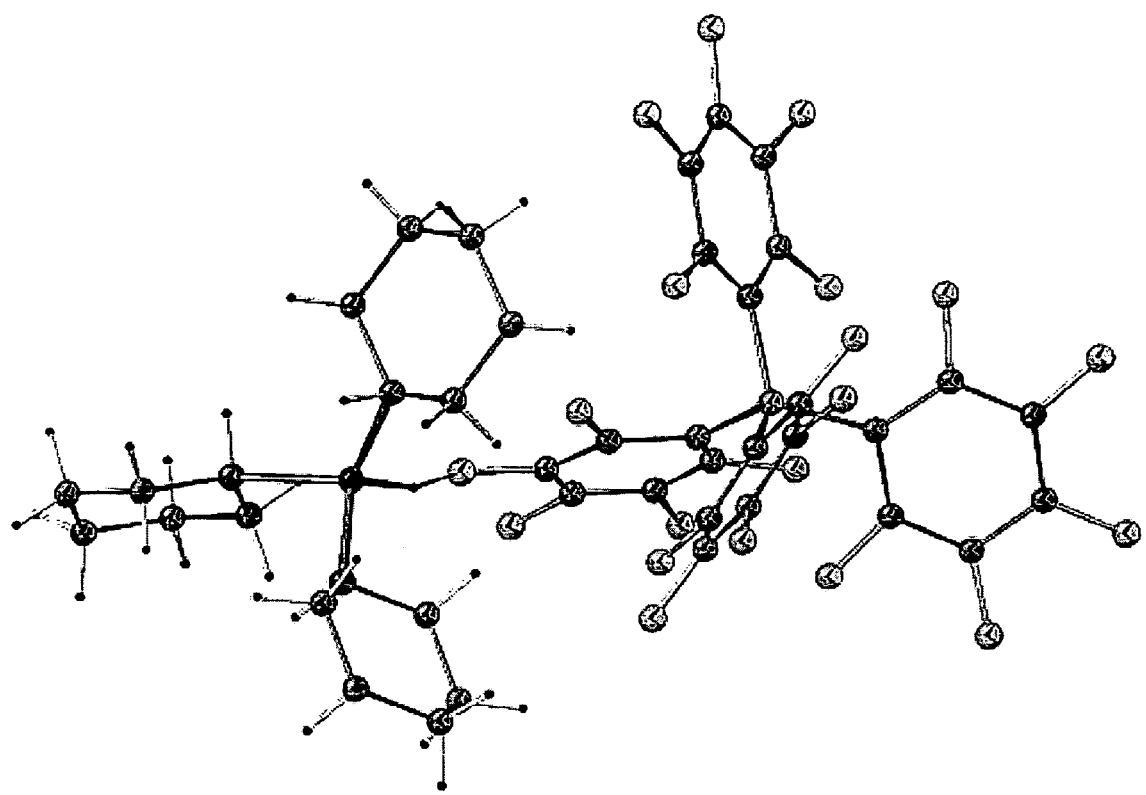
FIG. 1 is an X-ray crystallographic molecular structure of tricyclohexylphosphonium(tetrakispentafluorophenyl)borate.

The present invention will now be described more fully with reference to the accompanying drawings, in which exemplary embodiments of the invention are shown.

The present invention provides a method of preparing a phosphonium compound represented by Formula 1 below, contacting a phosphonium compound represented by Formula 2 below and a salt compound represented by Formula 3 below:

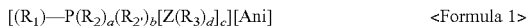

<Formula 1> wherein, a, b, and c are each an integer of 0 to 3 with proviso that a+b+c=3,

Z is oxygen, sulfur, silicon, or nitrogen, d is 1 when Z is oxygen or sulfur, is 2 when Z is nitrogen, and is 3 when Z is silicon, $R_1$ is hydrogen, alkyl, or aryl, $R_2$, $R_{2'}$, and $R_3$ are each independently hydrogen; straight or branched $C_{1-20}$ alkyl, alkoxy, aryloxy, allyl, alkenyl, or vinyl which is unsubstituted or substituted by a hydrocarbon(s), halogen(s) or $C_{1-20}$ haloalkyl; $C_{3-12}$ cycloalkyl which is unsubstituted or substituted by a hydrocarbon(s), halogen(s) or $C_{1-20}$ haloalkyl; $C_{6-40}$ aryl which is unsubstituted or substituted by a hydrocarbon(s), halogen(s) or $C_{1-20}$ haloalkyl; $C_{7-15}$ aralkyl which is unsubstituted or substituted by a hydrocarbon(s), halogen(s) or $C_{1-20}$ haloalkyl; $C_{3-20}$ alkynyl which is unsubstituted or substituted by a hydrocarbon(s), halogen(s) or $C_{1-20}$ haloalkyl; tri (straight or branched $C_{1-10}$ alkyl)silyl; tri(straight or branched $C_{1-10}$ alkoxy)silyl; tri($C_{3-12}$ cycloalkyl)silyl where the $C_{3-12}$ cycloalkyl moiety is unsubstituted or substituted by a hydrocarbon(s), halogen(s) or $C_{1-20}$ haloalkyl; tri($C_{6-40}$ aryl)silyl where the $C_{6-40}$ aryl moiety is unsubstituted or substituted by a hydrocarbon(s), halogen(s) or $C_{1-20}$ haloalkyl; tri($C_{6-40}$ aryloxy)silyl where the $C_{6-40}$ aryloxy moiety is unsubstituted or substituted by a hydrocarbon(s), halogen(s) or $C_{1-20}$ haloalkyl; tri(straight or branched $C_{1-10}$ alkyl)siloxy; tri($C_{3-12}$ cycloalkyl)siloxy where the $C_{3-12}$ cycloalkyl moiety is unsubstituted or substituted by a hydrocarbon(s), halogen(s) or $C_{1-20}$ haloalkyl; or tri($C_{6-40}$ aryl)siloxy where the $C_{6-40}$ aryl moiety is unsubstituted or substituted by a hydrocarbon(s), halogen(s) or $C_{1-20}$ haloalkyl, and

[Ani] is borate, aluminate, [$SbF_6$]—, [$PF_6$]—, [$AsF_6$]—, perfluoroacetate ([$CF_3CO_2$]—), perfluoropropionate ([$C_2F_5CO_2$]—), perfluorobutyrate ([$CF_3CF_2CF_2CO_2$]—), perchlorate ([$ClO_4$]—), p-toluenesulfonate ([p-$CH_3C_6H_4SO_3$]—), [$SO_3CF_3$]—, boratabenzene, or carborane which is unsubstituted or substituted by halogen(s),

<Formula 2> wherein H is hydrogen, X is a halogen atom, and $R_1$, $R_2$, $R_{2'}$, a, and b are as defined above, and

<Formula 3> wherein C is alkaline metal or MgX, and [Ani] is as defined above.

In more detail, in the preparation method for the phosphonium compound of Formula 1, the protic phosphonium compound of Formula 2 reacts with the salt compound of Formula 3 to produce the phosphonium compound of Formula 1, together with a [C][X]byproduct as a precipitate. The salt compound of Formula 3 is a salt compound of the [Ani] anion mainly containing alkaline metal or MgX (halo magnesium).

The reaction of the phosphonium compound of Formula 2 with the salt compound of Formula 3 may be performed in a solvent such as a hydrocarbon solvent (e.g., hexane), or a conventional organic solvent (e.g., dichloromethane, chloroform, tetrahydrofuran (THF), diethylether, benzene, toluene, or chlorobenzene). A halogen solvent such as dichloromethane, chloroform, or chlorobenzene is preferred. The reaction between the phosphonium compound of Formula 2 and the salt compound of Formula 3 may occur in a solution wherein both of two compounds are soluble in a solvent or in a slurry wherein one of them is insoluble in a solvent. During the reaction between the phosphonium compound of Formula 2 and the salt compound of Formula 3, a [C][X]is produced as a byproduct. The [C][X]is easily precipitated in a reaction solvent and removed through filtering, and thus, the phosphonium compound of Formula 1 can be obtained without further purification. The reaction temperature may be 0 to 100° C., and more preferably, room temperature.

The preparation method of the present invention may further include the preparation of the phosphonium compound of Formula 2 by treating a phosphine compound represented by Formula 4 below with an acid:

<Formula 4> wherein $R_1$, $R_2$, $R_{2'}$, a, and b are as defined above.

In more detail, the phosphonium compound of Formula 2 can be prepared by reacting the phosphine compound of Formula 4 with a protic acid. Here, the protic acid is an acid capable of acting as a H+ donor, e.g., HCl, HBr, HI, HF, or $HPF_6$. The protic acid is not particularly limited and may be any acid commonly used in the art. The reaction between the phosphine compound of Formula 4 and the protic acid may be performed in a solvent such as hydrocarbon (e.g., hexane) and ether to produce the protic phosphonium compound of Formula 2 as a precipitate. Thus, the protic phosphonium compound of Formula 2 can be obtained without further purification. The reaction temperature may be 0 to 100° C., more preferably, room temperature.

In the phosphonium compound of Formula 1, the borate or the aluminate of [Ani] may be an anion represented by Formula 1A or 1B below:

    <Formula 1A>

    <Formula 1B> wherein M' is boron or aluminum, and $R_4$'s are each independently halogen; straight or branched $C_{1-20}$ alkyl or alkenyl which is unsubstituted or substituted by a hydrocarbon(s), halogen(s) or $C_{1-20}$ haloalkyl; $C_{3-12}$ cycloalkyl which is unsubstituted or substituted by a hydrocarbon(s), halogen(s) or $C_{1-20}$ haloalkyl; $C_{6-40}$ aryl which is unsubstituted or substituted by a hydrocarbon(s), halogen(s) or $C_{1-20}$ haloalkyl; $C_{6-40}$ aryl which is substituted by straight or branched $C_{3-20}$ trialkylsiloxy or straight or branched $C_{18-48}$ triarylsiloxy; or $C_{7-15}$ aralkyl which is unsubstituted or substituted by a hydrocarbon(s), halogen(s) or $C_{1-20}$ haloalkyl.

A cocatalyst compound prepared according to the preparation method of the present invention can be used in addition polymerization of cyclic olefin monomers.

A catalyst system including a cocatalyst compound prepared according to the preparation method of the present invention has good thermal and chemical stability, and thus, can prevent deactivation of the catalyst due to polar functional groups of monomers. Therefore, a high molecular weight polymer can be prepared at high yield, and the amount of the catalyst relative to a monomer can be reduced, whereby removal of a catalyst residue is not required.

A catalyst system, including a cocatalyst compound prepared according to the preparation method of the present invention, may include a Group X organometallic compound represented by Formula 5 below as a precatalyst, and the phosphonium compound of Formula 1 as a cocatalyst. The precatalyst has high stability against a monomer having a polar functional group. The cocatalyst can stabilize the catalyst system with the phosphonium and prevent the deactivation of the catalyst against a polar functional group of a polar monomer, compared to ammonium borate used as a conventional cocatalyst.

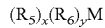    <Formula 5> wherein M is a Group X metal, x and y are each 0 to 2, and $R_5$ and $R_6$ are each independently hydrogen; halogen; straight or branched $C_{1-20}$ alkyl, $C_{6-20}$ aryl, $C_{7-20}$ aralkyl, or $C_{2-20}$ alkenyl; straight, cyclic, or branched $C_{1-20}$ alkyl, $C_{6-20}$ aryl, $C_{1-20}$ alkoxy, carboxyl, amine, $C_{7-20}$ aralkyl, or $C_{2-20}$ alkenyl including an atom or a functional group selected from the group consisting of halogen(s), hetero atom(s) (e.g., Si, Ge, S, O, or N), alkyl, alkenyl, and alkynyl; straight or branched $C_{1-20}$ haloalkyl, $C_{1-20}$ haloalkenyl, $C_{3-20}$ haloalkynyl, or $C_{6-40}$ haloaryl which is unsubstituted or substituted by a hydrocarbon(s).

In more detail, a method of preparing a cyclic olefin polymer having a polar functional group using a catalyst system including a cocatalyst compound prepared according to the preparation method of the present invention includes: preparing a catalyst mixture including a precatalyst containing a Group X metal represented by Formula 5 and a cocatalyst containing a phosphonium compound represented by Formula 1; and performing addition polymerization of a monomer solution including a cyclic olefin monomer having at least one polar functional group in the presence of the catalyst mixture at a temperature of 80 to 150° C.

A catalyst system including a cocatalyst prepared according to the preparation method of the present invention is thermally stable so that it is not thermally decomposed at a temperature of 80° C. or more, and thus, hinders an interaction between a polar functional group of a cyclic olefin monomer and a cationic catalyst at high temperature. Therefore, a catalytic active site can be formed or activated, thereby resulting in high-yield production of a high molecular weight cyclic olefin polymer having at least one polar functional group. If the polymerization temperature exceeds 150° C., the activity of the catalyst component may be lowered due to thermal decomposition of the catalyst component, which makes it difficult to prepare at least one polar functional group-containing cyclic olefin polymer with high molecular weight.

The monomer used in the preparation method for at least one polar functional group-containing cyclic olefin polymer may be a norbornene-based monomer having at least one polar functional group. A cyclic norbornene-based monomer or a norbornene derivative refers to a monomer including at least one norbornene (bicyclo[2.2.1]hept-2-ene) unit.

The polar functional group-containing cyclic olefin addition polymer may be a homopolymer prepared by addition polymerization of norbornene-based monomers having at least one polar functional group in the presence of the above-described catalyst mixture, a copolymer or terpolymer prepared by addition polymerization of different norbornene-based monomers having different polar functional groups, or a copolymer or terpolymer prepared by addition polymerization of a norbornene-based monomer having at least one polar functional group and another norbornene-based monomer having no polar functional group.

The polar functional group-containing norbornene-based monomer may be a compound represented by Formula 6 below:

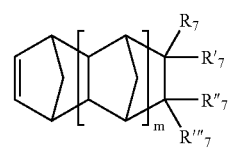    <Formula 6> wherein m is an integer of 0 to 4, and at least one of $R_7$, $R'_7$, $R''_7$, and $R'''_7$ is a polar functional group and the others are each a nonpolar functional group. $R_7$, $R'_7$, $R''_7$, and $R'''_7$ may be fused to form a saturated or unsaturated $C_{4-12}$ cyclic group or a $C_{6-24}$ aromatic ring. The nonpolar functional group is hydrogen; halogen; straight or branched $C_{1-20}$ alkyl, haloalkyl, alkenyl, or haloalkenyl; straight or branched $C_{3-20}$ alkynyl or haloalkynyl; $C_{3-12}$ cycloalkyl which is unsubstituted or substituted by alkyl, alkenyl, alkynyl, halogen, haloalkyl, haloalkenyl, or haloalkynyl; $C_{6-40}$ aryl which is unsubstituted or substituted by alkyl, alkenyl, alkynyl, halogen, haloalkyl, haloalkenyl, or haloalkynyl; or $C_{7-15}$ aralkyl which is unsubstituted or substituted by alkyl, alkenyl, alkynyl, halogen, haloalkyl, haloalkenyl, or haloalkynyl. The polar functional group is a non-hydrocarbonaceous polar group including at least one of oxygen, nitrogen, phosphorus, sulfur, silicon, and boron. The non-hydrocarbonaceous polar group may be selected from the group consisting of —$R^8OR^9$, —$OR^9$, —$C(O)OR^9$, —$R^8C(O)OR^9$, —$OC(O)OR^9$, —$R^8OC(O)OR^9$, —$C(O)R^9$, —$R^8C(O)R^9$, —$OC(O)R^9$, —$R^8OC(O)R^9$, —$(R^8O)_k$—$OR^9$, —$(OR^8)_k$—$OR^9$, —C(O)—O—C(O)R$^9$, —R$^8$C(O)—O—C(O)R$^9$, —SR$^9$, —R$^8$SR$^9$, —SSR$^8$, —R$^8$SSR$^9$, —S(=O)R$^9$, —R$^8$S(=O)R$^9$, —R$^8$C(=S)R$^9$, —R$^8$C(=S)SR$^9$, —R$^8$SO$_3$R$^9$, —SO$_3$R$^9$, —R$^8$N=C=S, —N=C=S, —NCO, R$^8$—NCO, —CN, —R$^8$CN, —NNC(=S)R$^9$, —R$^8$NNC(=S)R$^9$, —NO$_2$, —R$^8$NO$_2$, —P(R$^9$)$_2$, —R$^8$P(R$^9$)$_2$, —P(=O)(R$^9$)$_2$, —R$^8$P(=O)(R$^9$)$_2$,
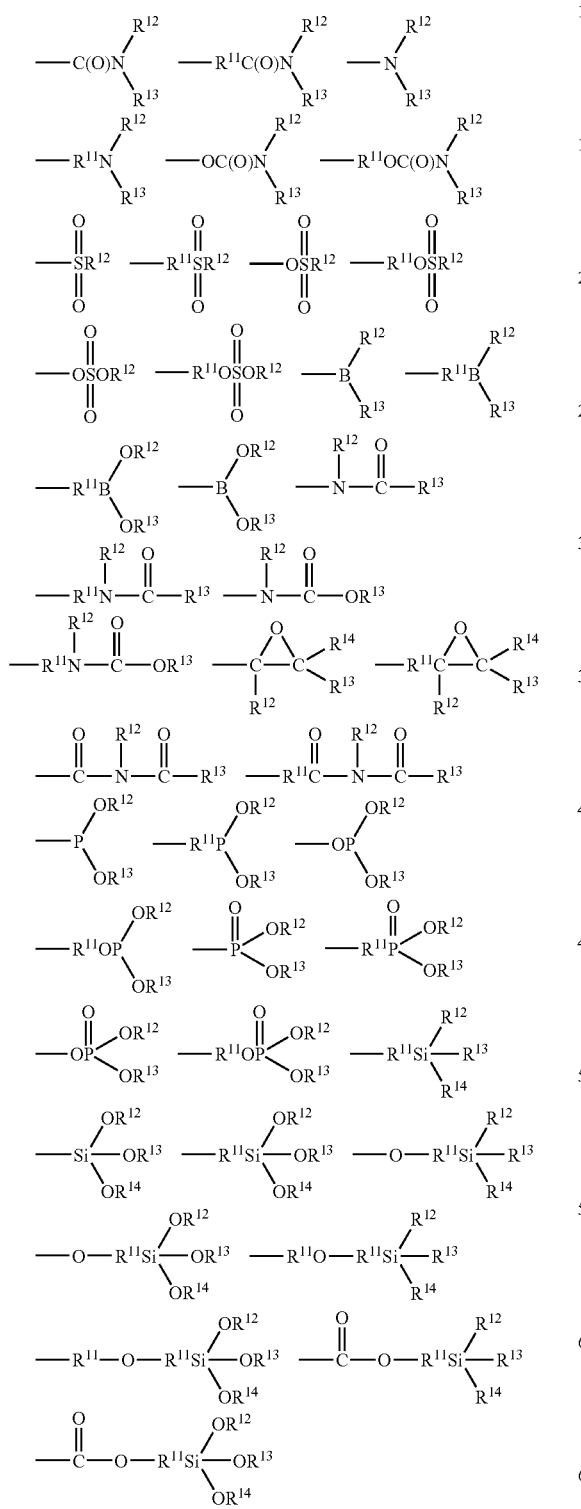
-continued
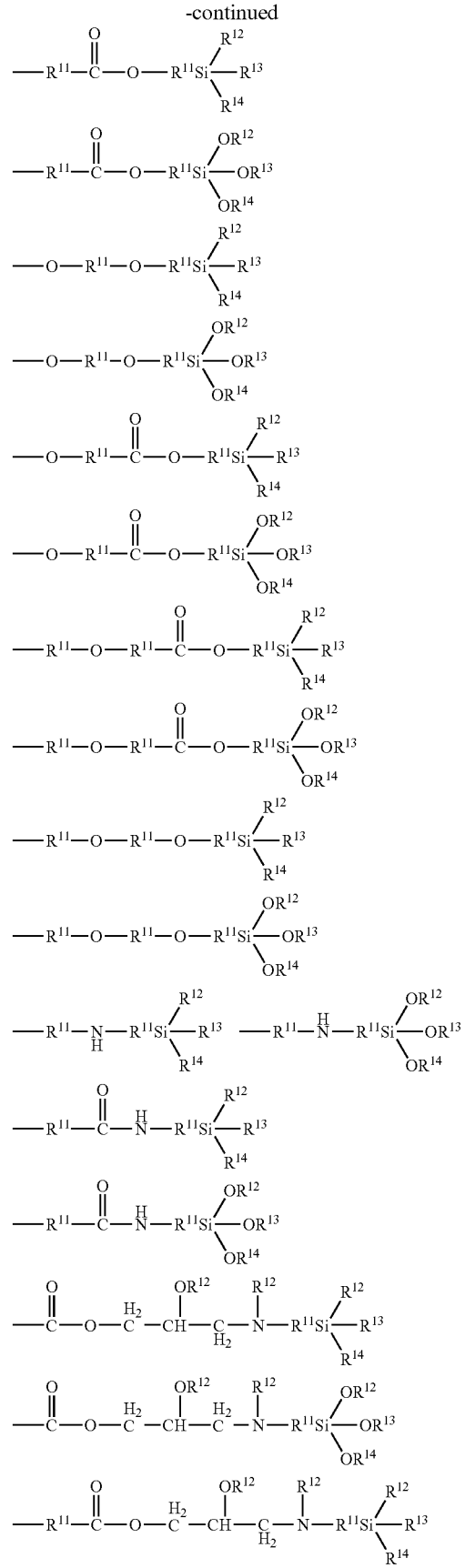

-continued

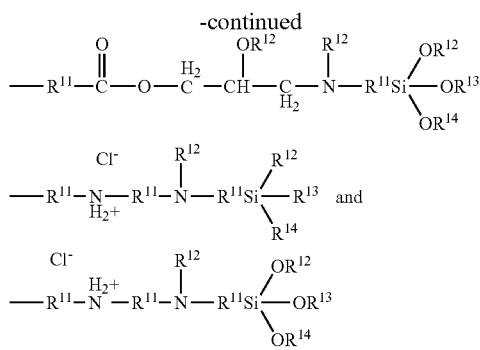

where $R^8$'s and $R^{11}$'s are each straight or branched $C_{1-20}$ alkylene, haloalkylene, alkenylene, or haloalkenylene; straight or branched $C_{3-20}$ alkynylene or haloalkynylene; $C_{3-12}$ cycloalkylene which is unsubstituted or substituted by alkyl, alkenyl, alkynyl, halogen, haloalkyl, haloalkenyl, or haloalkynyl; $C_{6-40}$ arylene which is unsubstituted or substituted by alkyl, alkenyl, alkynyl, halogen, haloalkyl, haloalkenyl, or haloalkynyl; or $C_{7-15}$ aralkylene which is unsubstituted or substituted by alkyl, alkenyl, alkynyl, halogen, haloalkyl, haloalkenyl, or haloalkynyl, $R^9$'s, $R^{12}$'s, $R^{13}$'S, and $R^{14}$'s are each hydrogen; halogen; straight or branched $C_{1-20}$ alkyl, haloalkyl, alkenyl, or haloalkenyl; straight or branched $C_{3-20}$ alkynyl or haloalkynyl; $C_{3-12}$ cycloalkyl which is unsubstitued or substituted by alkyl, alkenyl, alkynyl, halogen, haloalkyl, haloalkenyl, or haloalkynyl; $C_{6-40}$ aryl which is unsubstituted or substituted by alkyl, alkenyl, alkynyl, halogen, haloalkyl, haloalkenyl, or haloalkynyl; $C_{7-15}$ aralkyl which is unsubstituted or substituted by alkyl, alkenyl, alkynyl, halogen, haloalkyl, haloalkenyl, or haloalkynyl; alkoxy; haloalkoxy; carboxyl; or halocarboxyl, and k is an integer of 0 to 10.

In the preparation method for the polar functional group-containing cyclic olefin polymer, the molar ratio of the cocatalyst to the precatalyst containing the Group X transition metal may be 0.5-10 to 1. If the molar ratio of the cocatalyst relative to the precatalyst is less than 0.5, the precatalyst may be insignificantly activated. On the other hand, if the molar ratio of the cocatalyst relative to the precatalyst is more than 10, a stereo-specific hindrance and excess stabilization of catalytically active cationic species may be caused by the coordination of excess of the phosphonium to the metal of the precatalyst to weaken the interaction between the catalyst and a double bond of the monomer, resulting in reducing yield and molecular weight of a product.

In the preparation method for the polar functional group-containing cyclic olefin polymer, the catalyst mixture may be loaded on a microparticle support. The microparticle support may be silica, titania, silica/chromia, silica/chromia/titania, silica/alumina, aluminum phosphate gel, silanized silica, silica hydrogel, montmorillonite clay, or zeolite. The use of the catalyst mixture loaded on the microparticle support enables to adjust a molecular weight distribution of the polymer according to a specific application of the polymer and to enhance an apparent density of the polymer.

The catalyst mixture can be directly introduced to a solid phase without using a solvent. Alternatively, an activated catalyst solution prepared by mixing the precatalyst and the cocatalyst in a solvent phase or two catalyst solutions prepared by dissolving the precatalyst and the cocatalyst in respective solvents can also be used for the polymerization. A solvent capable of solubilizing the precatalyst and the cocatalyst may be dichloromethane, dichloroethane, toluene, chlorobenzene, or a mixture thereof.

The content of an organic solvent used in the polymerization reaction may be 50 to 800 parts by weight, preferably 50 to 400 parts by weight, based on the total weight (100 parts by weight) of the monomer in the monomer solution. If the content of the organic solvent is less than 50 parts by weight, stirring may be difficult and the monomer may remain unreacted due to too high viscosity, thereby lowering a product yield. Furthermore, the use of excess solvent to decrease the viscosity of the reaction solution may render commercialization difficult. On the other hand, if the content of the organic solvent exceeds 800 parts by weight, the reaction rate may be lowered, thereby resulting in a reduction in yield and molecular weight of a product.

The catalyst mixture may be a metal catalyst complex composed of the precatalyst and the cocatalyst. The molar ratio of the precatalyst component in the catalyst mixture to all the monomers in the monomer solution may be 1/2,500 to 1/200,000, more preferably, 1/5000 to 1/20000. That is, even though the catalyst mixture is used in a much less amount compared to a conventional catalyst system, a cyclic olefin polymer, especially a norbornene-based polymer, having at least one polar functional group can be obtained at high yield.

At least one polar functional group-containing norbornene addition polymer prepared according to the preparation method for at least one polar functional group-containing cyclic olefin polymer may include 0.1-99.9 mole % of at least one polar functional group-containing norbornene-based monomer. At this time, the polar functional group-containing norbornene-based monomer may be a mixture of an endo isomer and an exo isomer, and the mixture ratio of the endo isomer and the exo isomer is not limited.

The preparation method for the polar functional group-containing cyclic olefin polymer can be performed in the same manner as a conventional method of preparing a norbornene-based polymer including: mixing a norbornene-based monomer and a catalyst in a solvent and performing polymerization of the resultant mixture. According to the above-described method, a polar functional group-containing cyclic olefin polymer can be obtained at high yield of at least 40%, and can have a high weight average molecular weight ($M_w$) of 100,000 or more. A polar functional group-containing cyclic olefin polymer used as a material for optical films may be adjusted to have Mw of 100,000 to 1,000,000.

A functional group-containing norbornene-based polymer prepared according to the above-described method is transparent, and has good adhesion to metals or polymers having different polar functional groups, low dielectric constant suitable for insulating electronic devices, and good thermal stability and strength. Furthermore, the functional group-containing norbornene-based polymer has an adhesion to electronic substrates in the absence of a coupling agent and a good adhesion to metal substrates such as copper, silver, or gold. Still furthermore, the functional group-containing norbornene-based polymer has good optical characteristics and thus can be used as materials for protection films of polarization plates. In addition, the functional group-containing norbornene-based polymer can be used as materials for electronic devices such as integrated circuits, printed circuit boards, or multichip modules.

Meanwhile, the general conformational unit of cyclic olefins has one or two stable rotational states. Thus, cyclic olefins can have an extended conformation, like polyimides whose main chains are rigid phenyl rings. The introduction of polar functional groups to cyclic olefin polymers having such an extended conformation increases an intermolecular interaction, compared to simple cyclic olefin polymers. Therefore, intermolecular packing has a directional order, and thus, the cyclic olefin polymers can have optical and electrical anisotropy.

Hereinafter, the present invention will be described more specifically with reference to the following working examples. The following working examples are for illustrative purposes and are not intended to limit the scope of the invention.

In the following working examples, all manipulations for treating compounds susceptible to air or water were carried out using standard Schlenk technique or dry box technique. NMR spectra were obtained using a Bruker 600 spectrometer. The molecular weights and molecular weight distributions of polymers were measured using a GPC (gel permeation chromatography) system (Waters) using standard polystyrene samples. Toluene and diethylether were purified by distillation from potassium/benzophenone, and dichloromethane and chlorobenzene were purified by distillation from $CaH_2$, prior to the use of the solvents.

EXAMPLE 1

Preparation of $(Cy)_3PHCl$ $(Cy)_3P$ (2.02 g, 7.2 mmol, Cy=cyclohexyl) was added to a 250 mL Schlenk flask, and diethylether (150 mL) was added thereto. Then, anhydrous HCl (14.4 mL, 1.0M in ether) was added to the flask at room temperature, and the reaction mixture was incubated for about 20 minutes. The resultant white precipitate was filtered through a glass filter and washed three times with diethylether (80 mL), and a residual solvent was removed under vacuum at room temperature to give $(Cy)_3PHCl$ (86%, 1.95 g).

$^1$H-NMR (600 MHz, $CD_2Cl_2$): δ7.02~6.23 (d, 1H, $J_{H-P}$=470 Hz), 2.56~1.30 (m, 33H); $^{13}$C-NMR (600 MHz, $CD_2Cl_2$): δ28.9 (d), 28.5 (d), 26.8 (d), 25.6 (s). $^{31}$P-NMR (600 MHz, $CD_2Cl_2$): δ 22.98 (d, $J_{P-H}$=470 Hz).

EXAMPLE 2

Preparation of $(n-Bu)_3PHCl$ $(n-Bu)_3P$ (2.0 g, 10.0 mmol, n-Bu=n-butyl) was added to a 250 mL Schlenk flask, and diethylether (100 mL) was added thereto. Then, anhydrous HCl (20.0 mL, 1.0M in ether) was added to the flask at room temperature, and the reaction mixture was incubated for about 20 minutes. The resultant white precipitate was filtered through a glass filter and washed with diethylether (80 mL), and a residual solvent was removed under vacuum at room temperature to give $(n-Bu)_3PHCl$ (90%, 2.15 g).

EXAMPLE 3

Preparation of $[(Cy)_3PH][B(C_6F_5)_4]$

The $(Cy)_3PHCl$ (0.56 g, 1.75 mmol) prepared in Example 1 and $[Li][B(C_6F_5)_4]$ (1.0 g, 1.46 mmol) were added to respective Schlenk flasks (with capacity of 100 mL) in a glove box, and dichloromethane (20 mL) was added thereto. Then, the $(Cy)_3PHCl$ solution was gradually dropwise added to the $[Li][B(C_6F_5)_4]$ solution at room temperature. After one hour reaction, unreacted reactants were filtered out through a glass filter and a solvent was removed under vacuum to give $[(Cy)_3PH][B(C_6F_5)_4]$ (90%, 1.26 g).

$^1$H-NMR (600 MHz, $CD_2Cl_2$): δ5.32~4.65 (d, 1H, $J_{H-P}$=440 Hz), 2.43~1.33 (m, 33H); $^{13}$C-NMR (600 MHz, $CD_2Cl_2$): δ149.7, 148.1, 139.7, 139.2, 138.1, 138.0, 137.8, 136.2, 125.1, 124.9, 29.0, 28.8, 26.7 (d), 25.4 (s). $^{31}$P-NMR (600 MHz, $CD_2Cl_2$): 31.14 (d, $J_{P-H}$=440 Hz). $^{19}$F-NMR (600 MHz, $CD_2Cl_2$): −130.90, −161.51, −163.37.

Crystals suitable for X-ray diffraction analysis were obtained from a dichloromethane solution. The X-ray crystallographic molecular structure is illustrated in FIG. 1. Referring to FIG. 1, there exists a nonbonding interaction between the P atom of $[(Cy)_3PH]$ and the F atoms of $[B(C_6F_5)_4]$.

EXAMPLE 4

Preparation of $[(Cy)_3PH][B(C_6F_5)_4]$ $[(Cy)_3PH][B(C_6F_5)_4]$ was prepared in the same manner as in Example 3 except that $[Na][B(C_6F_5)_4]$ or $[MgBr][B(C_6F_5)_4]$ was used instead of $[Li][B(C_6F_5)_4]$. The product yield was about 90%, which was almost the same as that in Example 3.

EXAMPLE 5

Preparation of $[(n-Bu)_3PH][B(C_6F_5)_4]$

The $(n-Bu)_3PHCl$ (0.42 g, 1.75 mmol) prepared in Example 2 and $[Li][B(C_6F_5)_4]$ (1.0 g, 1.46 mmol) were added to respective Schlenk flasks (with capacity of 100 mL) in a glove box, and dichloromethane (20 mL) was added thereto. Then, the $(n-Bu)_3PHCl$ solution was gradually dropwise added to the $[Li][B(C_6F_5)_4]$ solution at room temperature. After one hour reaction, unreacted reactants were filtered out through a glass filter and a solvent was removed under vacuum to give $[(n-Bu)_3PH][B(C_6F_5)_4]$ (87%, 1.12 g).

EXAMPLE 6

Preparation of $[(t-Bu)_3PH][B(C_6F_5)_4]$ $(t-Bu)_3P$ (0.35 g, 1.73 mmol) was added to a 250 mL Schlenk flask, and diethylether (30 mL) was added thereto. Then, anhydrous HCl (1.9 mL, 1.0M in ether) was added to the flask at room temperature, and the reaction mixture was incubated for about 20 minutes. The resultant white precipitate was filtered through a glass filter and washed with diethylether (30 mL), and a residual solvent was removed under vacuum at room temperature to give $(t-Bu)_3PHCl$ as white solid.

The $(t-Bu)_3PHCl$ was dissolved in dichloromethane (10 mL). $[Li][B(C_6F_5)_4]$ (1.07 g, 1.56 mmol) was added to a 100 mL Schlenk flask in a glove box, and dichloromethane (20 mL) was added thereto. Then, the $(t-Bu)_3PHCl$ solution was gradually dropwise added to the $[Li][B(C_6F_5)_4]$ solution at room temperature. After one hour reaction, LiCl byproducts were filtered out through a glass filter and a solvent was removed under vacuum to give $[(t-Bu)_3PH][B(C_6F_5)_4]$ (67%, 1.05 g).

$^1$H-NMR (600 MHz, $CD_2Cl_2$): δ5.34~4.63 (d, 1H, $J_{H-P}$=440 Hz), 1.61 (d, 27H); $^{13}$C-NMR (600 MHz, $CD_2Cl_2$): δ149.5, 147.9, 139.6, 138.0, 137.7, 136.0, 124.4, 38.3, 30.4. $^{31}$P-NMR (600 MHz, $CD_2Cl_2$): 63.0 (d, $J_{P-H}$=440 Hz). $^{19}$F-NMR (600 MHz, $CD_2Cl_2$): −133.3, −163.9, −167.8.

EXAMPLE 7

Preparation of $[(Et)_3PH][B(C_6F_5)_4]$ $(Et)_3P$ (0.8 g, 6.77 mmol, Et=ethyl) was added to a 250 mL Schlenk flask, and diethylether (50 mL) was added thereto. Then, anhydrous HCl (7.4 mL, 1.0M in ether) was added to the flask at room temperature, and the reaction mixture was incubated for about 20 minutes to obtain a white precipitate. A solvent was removed under vacuum, the white precipitate was washed with hexane (30 mL), and a residual solvent was removed under vacuum at room temperature to give $(Et)_3$PHCl as white solid.

The $(Et)_3$PHCl was dissolved in dichloromethane (10 mL). $[Li][B(C_6F_5)_4]$ (4.41 g, 6.43 mmol) was added to a 100 mL Schlenk flask in a glove box, and dichloromethane (50 mL) was added thereto. Then, the $(Et)_3$PHCl solution was gradually dropwise added to the $[Li][B(C_6F_5)_4]$ solution at room temperature. After one hour reaction, LiCl byproducts were filtered out through a glass filter and a solvent was removed under vacuum to give $[(Et)_3PH][B(C_6F_5)_4]$ (54%, 2.91).

$^1$H-NMR (600 MHz, $CD_2Cl_2$): δ6.06 (m, 0.5H), 5.30 (m, 0.5H), 2.28 (m, 6H), 1.40 (m, 9H); $^{13}$C-NMR (600 MHz, $CD_2Cl_2$): δ149.5, 147.9, 139.7, 138.0, 137.9, 137.7, 136.1, 124.6, 10.6 (d), 6.8 (d). $^{31}$P-NMR (600 MHz, $CD_2Cl_2$): 26.3 (d). $^{19}$F-NMR (600 MHz, $CD_2Cl_2$): −133.5, −163.7, −167.8.

EXAMPLE 8

Preparation of 5-norbornene-2-carboxylic acid methyl ester polymer 5-norbornene-2-carboxylic acid methyl ester (10 mL, 55.6 mmol) was added to a 250 mL Schlenk flask. $Pd(OAc)_2$ (OAc=acetate, 2.5 mg, 11 μmol) and $[(Cy)_3PH][B(C_6F_5)_4]$ (21.1 mg, 22 μmol) were added to another 250 mL Schlenk flask, and 1 Ml of dichloromethane was added thereto. Then, the catalyst solution was dropwise added to the monomer-containing flask through a syringe. The reaction mixture was incubated at 90° C. for 10 hours, and 50 mL of toluene was added thereto to dissolve a polymer. Then, the reaction solution was added to excess ethanol to give a white polymer precipitate. The precipitate was filtered through a glass funnel and dried in a vacuum oven at 80° C. for 24 hours to give 8.4 g of 5-norbornene-2-carboxylic acid methyl ester polymer (80.5 wt % based on the total weight of the monomer). The Mw and Mw/Mn of the polymer was 204,000 and 2.02, respectively.

EXAMPLES 9-15

Preparation of 5-norbornene-2-methyl acetate polymers 5-norbornene-2-methyl acetate polymers were prepared with changing a molar ratio of Pd(OAc)2 to $[(Cy)_3PH][B(C_6F_5)_4]$ (2:1, 1:1, 2:3, 1:2, 1:4, 1:6, and 1:8). 5-norbornene-2-methyl acetate (4 mL, 24.7 mmol) and toluene (12 Ml) were added to a 100 Ml Schlenk flask to obtain a monomer solution, and $Pd(OAc)_2$ (1.1 mg, 4.9 μmol) and $[(Cy)_3PH][B(C_6F_5)_4]$ at various molar ratios were dissolved in dichloromethane (1 Ml) to obtain catalyst solutions. Each catalyst solution was added to the monomer solution, and the resultant mixtures were incubated at 90° C. for 4 hours while stirring. The polymerization and the polymer recovery were performed in the same manner as in Example 8 to give 5-norbornene-2-methyl acetate polymers. The yields, Mw, and Mw/Mn of some of the 5-norbornene-2-methyl acetate polymers are summarized in Table 1 below.

TABLE 1

| Sample | $Pd(OAc)_2$ (mg) | $[(Cy)_3PH][B(C_6F_5)_4]$ (mg) | Molar ratio of Pd/B | Yield [g] | Yield [%] | Mw | Mw/Mn |
|---|---|---|---|---|---|---|---|
| Example 9 | 1.1 | 2.4 | 2/1 | 1.77 | 43.2 | 333,400 | 2.11 |
| Example 10 | 1.1 | 4.7 | 1/1 | 3.52 | 86.0 | 272,800 | 2.28 |
| Example 12 | 1.1 | 9.5 | 1/2 | 3.83 | 93.4 | 256,300 | 2.49 |
| Example 13 | 1.1 | 19.0 | 1/4 | 3.80 | 90.5 | 221,600 | 2.45 |
| Example 14 | 1.1 | 28.4 | 1/6 | 3.39 | 82.7 | 194,100 | 2.25 |

EXAMPLE 16

Preparation of 5-norbornene-2-carboxylic acid methyl ester/norbornene addition copolymer A norbornene carboxylic acid methyl ester monomer (16.74 g), a norbornene monomer (4.44 g), and 37 Ml of toluene were added to a 250 Ml Schlenk flask. A solution of $Pd(OAc)_2$ (4.79 mg) and $[(Cy)_3PH][B(C_6F_5)_4]$ (40.4 mg) in dichloromethane (2 Ml) was added to the flask, and the reaction mixture was incubated at 90° C. for 10 hours while stirring. Then, the reaction solution was added to excess ethanol to obtain a white copolymer precipitate. The precipitate was filtered through a glass funnel and dried in a vacuum oven at 65° C. for 24 hours to give 14.86 g of a norbornene/5-norbornene-2-carboxylic acid methyl ester copolymer (yield: 70.2 wt % based on the total weight of the monomers). The Mw and Mw/Mn of the polymer were 184,000 and 2.12, respectively.

EXAMPLE 17

Preparation of 5-norbornene-2-carboxylic acid methyl ester/butyl norbornene addition copolymer A 5-norbornene-2-carboxylic acid methyl ester monomer (14.64 g), a butyl norbornene monomer (6.14 g), and toluene (37 Ml) were added to a 250 Ml Schlenk flask. A solution of $Pd(acac)_2$ (4.19 mg, acac=acetylacetonate) and $[(Cy)_3PH][B(C_6F_5)_4]$ (32.8 mg) in dichloromethane (2 Ml) was added to the flask, and the reaction mixture was incubated at 90° C. for 10 hours while stirring. Then, the reaction solution was added to excess ethanol to obtain a white copolymer precipitate. The precipitate was filtered through a glass funnel and dried in a vacuum oven at 65° C. for 24 hours to give a 13.7 g of butyl norbornene/5-norbornene-2-carboxylic acid methyl ester copolymer (yield: 65.9 wt % based on the total weight of the monomers). The Mw and Mw/Mn of the polymer were 157,000 and 2.13, respectively.

EXAMPLE 18

Preparation of 5-norbornene-2-methyl acetate/butylnorbornene addition copolymer (catalyst: Pd(acac)$_2$)

5-norbornene-2-methyl acetate (8.2 g), butylnorbornene (3.2 g), and toluene (36 Ml) were added to a 250 Ml Schlenk flask. A solution of Pd(OAc)$_2$ (3.2 mg) and [(Cy)$_3$PH][B(C$_6$F$_5$)$_4$] (27.0 mg) in dichloromethane (2 Ml) was added to the flask, and the reaction mixture was incubated at 90° C. for 4 hours. Then, the reaction solution was added to excess ethanol to obtain a white copolymer precipitate. The precipitate was filtered through a glass funnel and dried in a vacuum oven at 65° C. for 24 hours to give 9.30 g of a butylnorbornene/5-norbornene-2-methyl acetate copolymer (yield: 81.7 wt % based on the total weight of the monomers). The Mw and Mw/Mn of the polymer were 218,300 and 3.52, respectively.

COMPARATIVE EXAMPLE 1

Preparation of 5-norbornene-2-carboxylic acid polymer 10 g of 5-norbornene-2-carboxylic acid and 100 mg of [Pd(C$_6$H$_5$CN)Cl$_2$]$_2$ were added to a reaction flask, and the reaction mixture was incubated at 140° C. for 10.5 hours to give 5.75 g of a polymer. The Mw of the polymer was 1129.

COMPARATIVE EXAMPLE 2

Preparation of 5-norbornene-2-methyl-decanyl acetate polymer 5-norbornene-2-methyl-decanyl acetate (1.03 g, 3.7 mmol) was added to a Schlenk flask. [(Allyl)PdCl]$_2$ (13.15 mg, 3.60×10$^{-2}$ mmol) and AgSbF$_6$ (35 mg, 10.1×10$^{-2}$ mmol) were added to another Schlenk flask, and 2 mL of chlorobenzene was added thereto. An AgCl precipitate was filtered out from the catalyst solution, the remaining catalyst solution was dropwise added to the monomer-containing flask at room temperature, and the reaction proceeded for 24 hours. The yield and Mw of the titled polymer were 1.01 g (98%) and 58,848, respectively.

COMPARATIVE EXAMPLE 3

Preparation of 5-norbornene-2-methyl acetate polymer

Li[B(C$_6$F$_5$)$_4$] was added to 5-norbornene-2-methyl acetate (5.0 g, 30 mmol) in a Schlenk flask. A solution of [(Allyl)PdCl]$_2$ (0.55 mg, 0.0015 mmol) and P(Cy)$_3$ (0.84 mg, 0.0030 mmol) in 0.1 mL of toluene was dropwise added to the monomer-containing flask, and the reaction mixture was incubated at 65° C. for 4 hours to give 0.25 g (5%) of the titled polymer.

COMPARATIVE EXAMPLE 4

Preparation of 5-norbornene-2-methyl acetate polymer in the presence of catalyst system including Pd(OAc)2 and dimethylanilinium tetrakis(pentafluorophenyl)borate 5-norbornene-2-methyl acetate (5 mL, 30.9 mmol) and toluene (15 Ml) were added to a 250 Ml Schlenk flask. A solution of Pd(OAc)$_2$ (1.4 mg, 6.2 mol) and dimethylanilinium tetrakis(pentafluorophenyl)borate (10.9 mg, 13.6 mol) in dichloromethane (1 Ml) was added to the flask, and the reaction mixture was incubated at 90° C. for 18 hours while stirring. Then, the reaction solution was added to excess ethanol. However, no polymer precipitate was obtained.

According to a method of preparing a phosphonium compound of the present invention, a phosphonium compound used as a cocatalyst for the preparation of polar cyclic olefin polymers can be produced at high yield.

What is claimed is:

1. A method of preparing a phosphonium compound represented by Formula 1 below, comprising contacting a phosphonium compound represented by Formula 2 below and a salt compound represented by Formula 3 below:

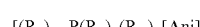   <Formula 1> wherein, a and b are each an integer of 0 to 3 with proviso that a+b=3,

R$_1$ is hydrogen, alkyl, or aryl,

R$_2$ and R$_{2'}$ are each independently hydrogen; straight or branched C$_{1-20}$ alkyl, alkoxy, allyl, alkenyl, or vinyl; C$_{3-12}$ cycloalkyl which is unsubstituted or substituted by a hydrocarbon(s), halogen(s) or C$_{1-20}$ haloalkyl; C$_{6-40}$ aryl which is unsubstituted or substituted by a hydrocarbon(s), halogen(s) or C$_{1-20}$ haloalkyl; C$_{7-15}$ aralkyl which is unsubstituted or substituted by a hydrocarbon(s), halogen(s) or C$_{1-20}$ haloalkyl; C$_{3-20}$ alkynyl which is unsubstituted or substituted by a hydrocarbon(s), halogen(s) or C$_{1-20}$ haloalkyl; tri(straight or branched C$_{1-10}$ alkyl)silyl; tri(straight or branched C$_{1-10}$ alkoxy)silyl; tri(C$_{3-12}$ cycloalkyl)silyl where the C$_{3-12}$ cycloalkyl moiety is unsubstituted or substituted by a hydrocarbon(s), halogen(s) or C$_{1-20}$ haloalkyl; tri(C$_{6-40}$ aryl)silyl where the C$_{6-40}$ aryl moiety is unsubstituted or substituted by a hydrocarbon(s), halogen(s) or C$_{1-20}$ haloalkyl; tri(C$_{6-40}$ aryloxy)silyl where the C$_{6-40}$ aryloxy moiety is unsubstituted or substituted by a hydrocarbon(s), halogen(s) or C$_{1-20}$ haloalkyl; tri(straight or branched C$_{1-10}$ alkyl)siloxy; tri(C$_{3-12}$ cycloalkyl)siloxy where the C$_{3-12}$ cycloalkyl moiety is unsubstituted or substituted by a hydrocarbon(s), halogen(s) or C$_{1-20}$ haloalkyl; or tri(C$_{6-40}$ aryl)siloxy where the C$_{6-40}$ aryl moiety is unsubstituted or substituted by a hydrocarbon(s), halogen(s) or C$_{1-20}$ haloalkyl, and

[Ani] is borate, aluminate, [SbF$_6$]—, [PF$_6$]—, [AsF$_6$]—, perfluoroacetate ([CF$_3$CO$_2$]—), perfluoropropionate ([C$_2$F$_5$CO$_2$]—), perfluorobutyrate ([CF$_3$CF$_2$CF$_2$CO$_2$]—), perchlorate ([ClO$_4$]—), p-toluenesulfonate ([p-$CH_3C_6H_4SO_3$]—), [$SO_3CF_3$]—, boratabenzene, or carborane which is unsubstituted or substituted by halogen(s), $$[(R_1)-P(R_2)_a(R_{2'})_b]HX \qquad \text{<Formula 2>}$$

wherein H is hydrogen, X is a halogen atom, and $R_1$, $R_2$, $R_{2'}$, a, and b are as defined above, and $$[C][Ani] \qquad \text{<Formula 3>}$$

wherein C is alkaline metal or MgX, and [Ani] is as defined above.

2. The method of claim 1, further comprising preparing the phosphonium compound of Formula 2 by treating a phosphine compound represented by Formula 4 below with an acid:

$$[(R_1)-P(R_2)_a(R_{2'})_b] \qquad \text{<Formula 4>}$$

wherein $R_1$, $R_2$, $R_{2'}$, a, and b are as defined in claim 1.

* * * * *